United States Patent [19]

Benninger et al.

[11] 3,962,348

[45] June 8, 1976

[54] ALIPHATIC AND CYCLIC PERFLUORO-ALKYL ETHERS AND PROCESS FOR THE PREPARATION THEREOF

[75] Inventors: Siegfried Benninger, Schwalbach, Taunus; Thomas Martini, Neuenhain, Taunus; Siegfried Rebsdat, Neuotting, all of Germany

[73] Assignee: Hoechst Aktiengesellschaft, Frankfurt am Main, Germany

[22] Filed: Feb. 7, 1974

[21] Appl. No.: 440,567

[30] Foreign Application Priority Data

Feb. 9, 1973 Germany............................ 2306494

[52] U.S. Cl............................ 260/615 F; 204/59 R; 204/81; 260/345.9; 260/347.8; 260/615 BF; 252/52 A; 252/54; 252/73; 252/77; 424/283; 424/285; 424/339; 424/341; 424/342

[51] Int. Cl.².......................................... C07L 43/12
[58] Field of Search.................... 260/615 F, 615 BF

[56] References Cited
UNITED STATES PATENTS

| | | | |
|---|---|---|---|
| 2,500,388 | 3/1950 | Simons | 260/615 F |
| 3,435,078 | 3/1969 | Nychka et al. | 260/615 |

*Primary Examiner*—Howard T. Mars
*Attorney, Agent, or Firm*—Curtis, Morris & Safford

[57] ABSTRACT

Mono- or polyhydric alcohols of the alkan-, tetrahydrofuran- or tetrahydropyran series or di- or trialkyleneglycols are dissolved in an aprotic polar solvent and reacted with $C_3F_6$ in the presence of trialkylamines, or with tetrafluoroethylene to give the corresponding tetrafluoroethyl- or hexafluoropropyl ethers. The solution of the fluoroethers in anhydrous hydrofluoric acid is electrolyzed. Hydrogen-free perfluoroethers are obtained.

4 Claims, No Drawings

ALIPHATIC AND CYCLIC PERFLUORO-ALKYL ETHERS AND PROCESS FOR THE PREPARATION THEREOF

The present invention relates to aliphatic and cyclic perfluoro-alkyl ethers and a process for the preparation thereof.

For the preparation of perfluoro-ethers, the following processes are known and applied:
1. Electrochemical fluorination of aliphatic hydrocarbon ethers according to Simons (see for example German Pat. No. 817,151).
2. Polymerization of perfluoro-propylene oxide or photochemical polymerization of perfluoro-propylene in the presence of oxygen (see for example British Pat. No. 1,217,871).
3. Formation reactions on the basis of preformed perfluoroalkyl ether compounds, for example by Wurtz-Fittig synthesis, starting from perfluoroalkoxy-alkylene iodides (see British Pat. No. 1,177,868), or, for example, by nucleophilic substitution reactions with perfluoro-alkoxides as nucleophilic agents (see U.S. Pat. No. 3,621,066).

As for the processes cited under 3), they result only in a relatively limited group of products, which is due to the small number of perfluoro-alkoxides and perfluoro-alkyl iodides available, such compounds being moreover comparatively expensive starting materials.

The processes cited under (2) give exclusively oligomeric and polymeric perfluoro-propylene oxides or perfluoro-ethylenepropylene oxide copolymers. Besides the relatively poor yields of the processes, the stabilization of the terminal groups of the products is one of the main problems: the terminal groups consist generally of carboxylic acid fluoride functions which have to be converted to chemically less reactive terminal groups by expensive and complicated methods (see for example German Offenlegungsschriften Nos. 2,131,749 and 1,668,395). On the whole, therefore, this is a troublesome process which results heterogeneous products having a widely varying polymerization degree; the products, moreover, require generally expensive multiple-step after-treatments.

From the above processes, the Simons process for the preparation of aliphatic perfluorinated ethers cited under (1) has been known for the longest time. However, it is also known that it is limited to relatively low molecular weight ethers, since the product yields especially of open-chain and multifunctional perfluorinated ethers, that is, those having several ether-oxygen bridges, rapidly drop to minimum values when there are more than 10 to 12 carbon atoms in the molecule. Furthermore, it is known that the product yields of perfluoro-α-alkyl derivatives of the tetrahydrofuran and tetrahydropyran series are somewhat higher than those of comparable open-chain analogs (see for example German Pat. No. 817,151, U.S. Pat. No. 2,644,823).

A serious disadvantage of the process, besides the mostly poor product yields, is a slow anode blocking by polymer material, which, because of an undesired side-reaction progressively concentrates in the electrolyte and on the anode surface with advancing process time (see Chem. Ing. Technik 37, 7, (1965)).

Recently, processes have been proposed which gave high yields of perfluorinated products by fluorination of α-perfluoroaryl substituted tetrahydrofurans (J. org. Chim. (russ.) 39, 2716 (1968)). However, because of the multiple-step and extremely expensive manufacturing processes of such perfluoro-aryl ethers, there is not much chance for an industrial utilization of this method.

A process has now been found for the preparation of aliphatic and cyclic perfluoro-alkyl ethers, which comprises dissolving
A. a mono- or polyfunctional alcohol having primary and/or secondary alcohol groups of the formulae (I) 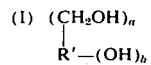

where R' is $C_nH_{2n+2-(a+b)}$, or

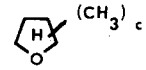

or

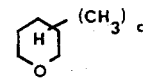

($a+b$) being free valencies,
$n$ being an integer of from 1 to 10, $c$ being an integer of from 0 to 3, $a$ and $b$ each being an integer of from 0 to 4, and ($a+b$) being an integer of 1 or more; or (II) $HO-[(CH_2)_d-CH_2-CHR''-O]_e H$ where R'' is H and $d$ is 0 to 4; or R'' is $CH_3$ and $d$ is 0; and $e$ is the integer of 2 or 3;

in an aprotic polar solvent, and converting them with hexafluoro-propene in the presence of trialkylamines, or with tetrafluoro-ethylene, at a temperature of from −30° to +100°C, to compounds of the formulae (III) 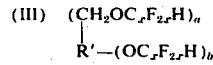

or (IV) 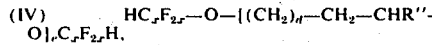

where $x$ is the integer 2 or 3 and the other symbols are as defined above, and by subsequently
B. dissolving the compounds of the formulae III or IV in anhydrous hydrofluoric acid, and electrolyzing the solution at a temperature of from −20° to +30°C and a voltage of from 4 to 7.5 volts, thus converting them to their perfluoroanalogs of the formulae (V) 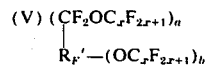

or (VI) $C_rF_{2r+1}-O-[(CF_2)_a-CF_2-CFR'\lambda_F-O]_cC_rF_{2r+1}$ where $R'_F$ is $C_nF_{2n+2-(a+b)}$ or

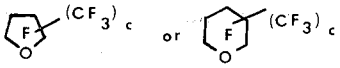

$R''_F$ is F and $d$ an integer of from 0 to 4, or $R''_F$ is $CF_3$ and $d$ is 0, and the other symbols $a$, $b$, $c$, $e$ and $n$ being as defined above.

The process of the invention gives extraordinary high yields of perfluorinated products. The process in any case gives yields which are far superior to those obtained in the processes starting from fluorine-free analogs or other isomeric hydrocarbon ethers having the same number of carbon atoms. Moreover, the principle of the process of the invention makes it possible to obtain high molecular weight perfluorinated ethers hitherto unknown which, because of the extraordinary adaptability and flexibility of their product properties, especially the boiling and solidification points, but also the viscosity, are a valuable addition to the present range of perfluorinated aliphatic ethers.

The process of the invention for the preparation of perfluorinated ethers comprises subjecting tetrafluoroethylene or hexafluoro-propene adducts of aliphatic or cyclic alcohols to electrofluorination according to known methods. The process of this invention may be applied to primary, secondary, mono- or polyfunctional alcohol-perfluoroolefin adducts.

By the preparation according to this invention of multifunctional primary perfluoro-alkyl ethers of formula V, especially compounds corresponding to $(C_nF_{2n+2-a}) - [CF_2O(C_rF_{2r+1})]_a$, where $n$ is from 1 to 10, $a$ from 1 to 4 and $x$ is 2 or 3 may be obtained which are prepared in accordance with the present invention from alcohols of the formula $(C_nH_{2n+2-a})-(CH_2OH)_a$ via their tetrafluoro-ethylene or hexafluoropropene adducts of the formula $(C_nH_{2n+2-a})-[(CH_2O(C_xF_{2x})H]_a$ with subsequent electrofluorination, among them preferably the compound where $n$ is 1 and $a$ is 4, corresponding to $C(CF_2OC_xF_{2x+1})_4$, from $C(CH_2OH)_4$ via $C[CH_2O(C_xF_{2x})H]_4$.

Among other compounds according to formula V, the process of the invention opens furthermore the whole range of the polyvalent secondary perfluoro-propyl ethers up to the perfluorohexapropyl-hexitol series. Thus, for example, the totality of the polyvalent ethers of formula V, where $n$ is from 3 to 6, $a$ is 2 and $b$ from 1 to 4, may be prepared from the tripropylglycerol ether via the corresponding erythritol to hexapropylsorbitol ethers, for example $CF_2OC_3F_7$
$(CF OC_3F_7)_m$
$CF_2OC_3F_7$, where $m$ is from 1 to 4.

Between the propyl ethers of monohydric secondary alcohols and those of the homologous glycerol series, there is the range of the alkyl substituted multivalent ethers, the exclusively secondary ones as well as those having primary and secondary ether functions in the molecule, which range is also included in the scope of the present invention. An example of this type is the perfluoro-propyleneglycol-dipropyl ether.

Furthermore, also the preparation of secondary perfluoroalkyl ethers, especially perfluoro-propyl ethers, is included in the scope of this invention. Thus, for example, perfluoroisopropyl-n-propyl ethers and isobutyl-n-propyl ethers may be prepared by electrofluorination of $(CH_3)_2CHOCF_2CFHCF_3$ or $C_2H_5CH(CH_3)OCF_2CFHCF_2$.

Furthermore, the process of the invention brings about an extraordinary progress in the preparation of multifunctional perfluoro-polyalkylene oxides of the formula VI which are hitherto unknown. To the preparation of known polymeric perfluoroethylene and -isopropylene oxides, there is thus added that of the oligomeric propylene to hexamethylene oxides which may have terminal perfluoro-ethyl or -propyl groups. Also branched alkylene oxides such as oligomeric propylene oxide, in the form of their $\alpha,\omega$-ditetrafluoro-ethylene and -dihexafluoropropene adducts, can be converted to their perfluorinated analogs without any difficulty. As an example $C_3F_7O(CF_2CFO)_3C_3F_7$
     $|$
    $CH_3$ may be cited. Generally preferred is the preparation of compounds of formula VI where $R''_F$ is F and $d$ is 2, or $R''_F$ is CF and $d$ is 0.

It is known from the literature that in the so-called Simons process the fluorination reaction as such is accompanied by side-reactions which may be cracking as well as polymerization reactions. As already mentioned above, these side-reactions are a serious disadvantage of the process, since not only do they drastically reduce the yield of the desired fluorination product with progressive molecule size, but also considerably complicate a continuous operation of the process by anode inhibition. The process of the invention brings about a very substantial progress over the state of the art inasmuch as, surprisingly, polymerization reactions are completely suppressed by using the cited perfluoro-olefin adducts of aliphatic alcohols. This can be easily proved by analysis of the electrolyte solution after the end of the process; but most important is the fact that the full activity of the electrodes is maintained for an unlimited time.

It is characteristic of electrofluorination reactions that they do not supply uniform products, but mixtures of perfluorinated substances which contain isomers and degradation products and also high molecular weight compounds besides the main product. It is one of the advantages of the process of the invention that a substantially higher product specificity is attained than in the case of fluorinating fluorine-free analogs. Moreover, there are absolutely no dimerization products and no high molecular weight by-products, which effect could be proved in several cases by corresponding parallel fluorinations. Thus, for example, the $C_2F_5OC_2F_4OC_2F_4OC_2F_5$ content in the fluorination product of $C_2H_5OC_2H_4OC_2H_4OC_2H_5$ is 55%, but it is 90%, when the starting material is $HC_2F_4OC_2F_4OC_2H_4OC_2F_4H$ (the percentages are area portions in the corresponding gas chromatograms).

Apart from the extraordinary utility of the process in practice — on account of the mechanisms described above —, the product yields, relative to the product amount to be expected according to the reaction equation, are in most cases considerably higher than those of the perfluorinated ethers prepared according to the state of the art from fluorine-free starting products.

The electrofluorination process in accordance with the present invention not only ensures practically extraordinary increases of yield as compared to the state of the art, but also, quite surprisingly, the attainment of a whole series of hitherto unknown perfluorinated ethers, which on the whole are very interesting for industrial practice where they close a gap open in many respects.

The products V and VI of the invention exhibit a wide range of physical properties; they offer the advantage that, by means of a corresponding substitution, the essential values such as boiling point, solidification point and viscosity may be influenced to a large extent.

The present invention provides furthermore novel perfluoroethyl and -propyl ethers having the following formulae

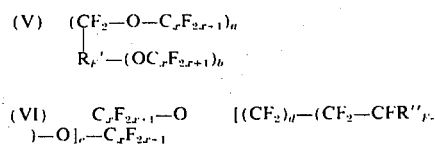

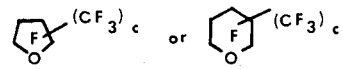

where $R'_F$ is $C_nF_{2n+2-(a+b)}$ or

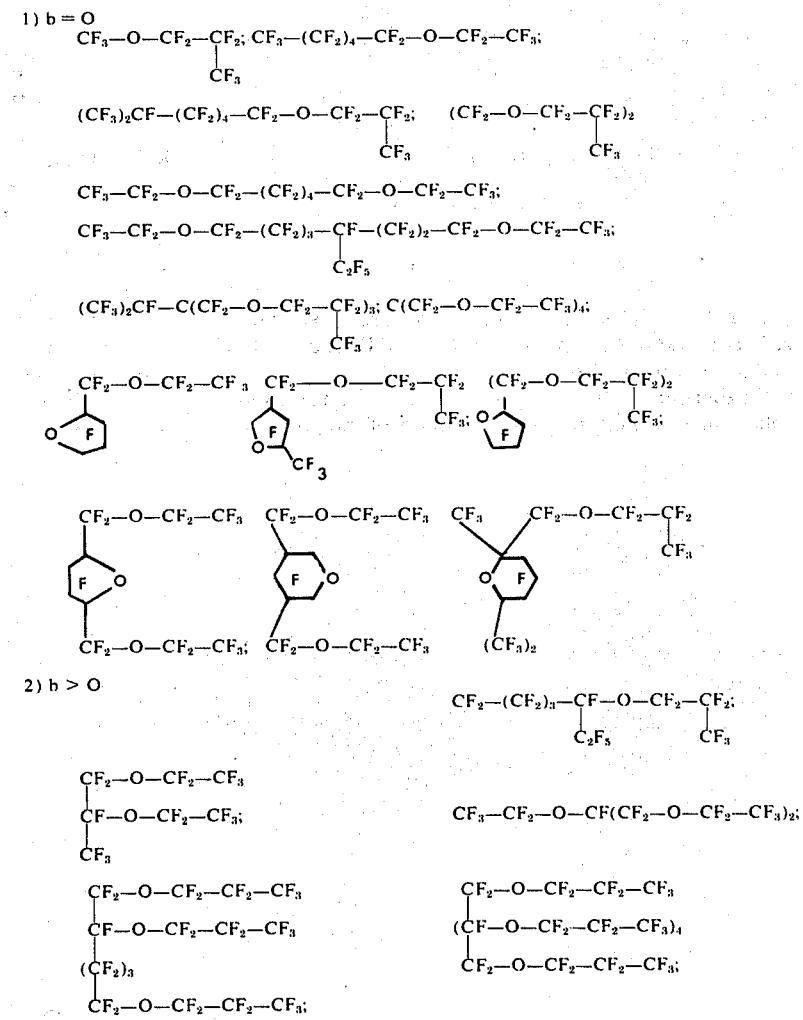

$R''_F$ is F and $d$ an integer of from 0 to 4, or $R''_F$ is $CF_3$ and $d$ is 0; $n$ being an integer of from 1 to 10, $a$ and $b$ each being an integer of from 0 to 4 ($a + b$ being 1 or more), $c$ an integer of from 0 to 3, $e$ and $x$ each being the integer of 2 or 3. Especially interesting are compounds where $n$ is from 1 to 5. The already known compounds perfluoro-diethyl and -di-n-propyl ether, and perfluoro-α-propoxymethylene-tetrahydrofuran are excepted.

Examples of those novel compounds are the following:

a. Compounds of formula V:

-continued

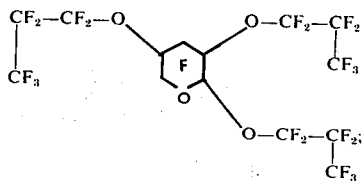
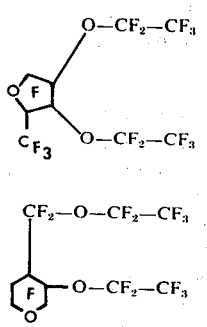

Preferred compounds of formula V are:

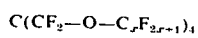

wherein $x$ is 2 or 3, and

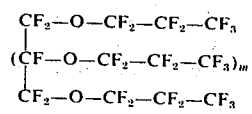

wherein $m$ is from 1 to 4.

b. Compounds of formula VI:

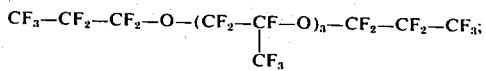

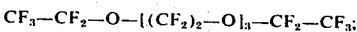

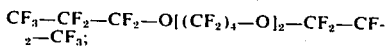

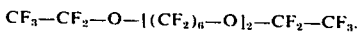

Preferred compounds of formula VI are those where $R''_F$ is F and $d$ is 2; and where $R''_F$ is $CF_3$ and $d$ is 0; $e$ and $x$ each being 2 or 3.

Furthermore, the present invention relates to the following novel intermediate products of the process of the invention, which products correspond to the following formulae:

(III) 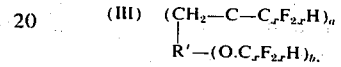

(IV) 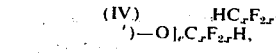

where R' is

or

R" is H and $d$ is an integer of from 0 to 4; or R" is $CH_3$ and $d$ is 0, $n$ being an integer of from 1 to 10 and $b$ being an integer of from 0 to 4, $a + b$ being an integer of 1 or more, $c$ being an integer of from 0 to 3, $e$ and/or $x$ being the integer of 2 or 3.

Of the intermediate products of the invention according to formula (III), those where $b$ is greater than 0, $X$ is 2 and R' is $C_nH_{2n+2-(a+b)}$, and those where $b$ is 0, $x$ is 2 or 3 and R' is $C_nH_{2n+2-(a+b)}$ are excepted.

The following compounds may be cited as examples:

a. Compounds of formula III:

1) b = 0

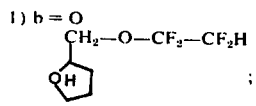 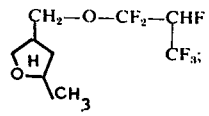 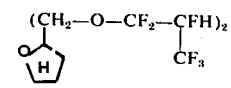

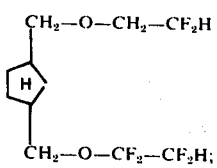 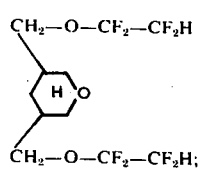 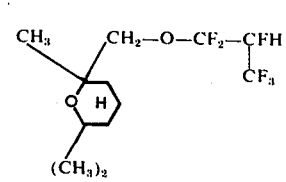

2) b > 0

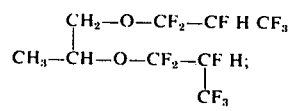

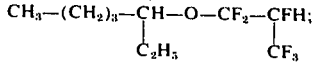

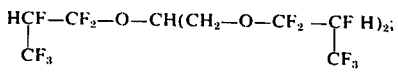

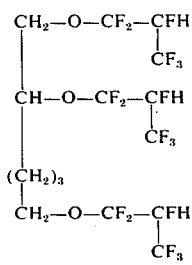

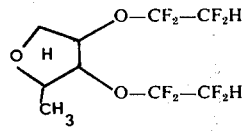

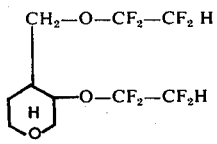

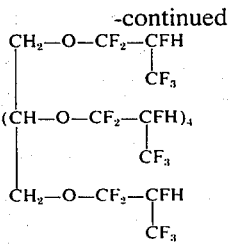

-continued

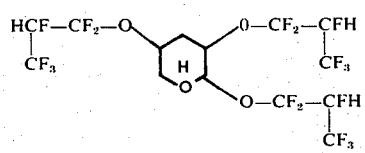

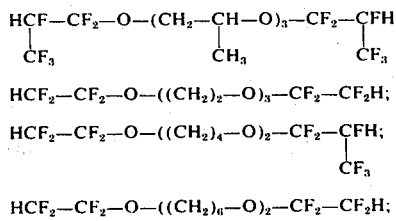

Preferred compounds of formula III are:

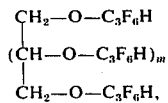

where $m$ is from 1 to 4.

b. Compounds of formula IV:

$$HCF-CF_2-O-(CH_2-CH-O)_3-CF_2-CFH$$
$$\phantom{HCF-CF_2-O-(CH_2-}CF_3\phantom{-O)_3}CH_3\phantom{-CF_2-}CF_3$$

$HCF_2-CF_2-O-((CH_2)_2-O)_3-CF_2-CF_2H;$ $HCF_2-CF_2-O-((CH_2)_4-O)_2-CF_2-CFH;$
$\phantom{HCF_2-CF_2-O-((CH_2)_4-O)_2-CF_2-}CF_3$ $HCF_2-CF_2-O-((CH_2)_6-O)_2-CF_2-CF_2H;$ Preferred compounds of formula IV are those where R'' is H and $d$ is 2, or R'' is $CH_3$ and $d$ is 0; $e$ and $x$ each being 2 or 3.

The substances V and VI of the invention have in common an excellent chemical stability which makes them thermally stable up to very high temperature ranges, stable to oxygen, fluorine or other extremely aggressive chemicals. They react even with sodium only at elevated temperatures. Moreover, they have a very poor dissolving power for usual solvents, and also for plastics of all kinds. Especially the latter property enables them to be advantageously applied as heat conductor liquids in the processing of polyolefins to shaped articles (see U.S. Pat. No. 3,655,480).

The cited properties ensure a wide application field for these products as reaction media, sealing liquids, lubricants under extreme chemical conditions, turbine propellants or hydraulic liquids; the physical conditions being adaptable to the requirements over a wide range. Especially for applications in nuclear techniques or in many fields of chemical engineering, the liquids of the invention, because of their better chemical resistance, are superior to the different polypropylene oxide fluids containing residual hydrogen or keto or ester groups, which fluids hitherto dominated these application fields especially at boiling ranges above 180°–200°C.

Apart from the above applications, the substances have interesting properties as heat conductors, and also as cooling liquids; depending on the boiling range, the substances of formulae V and VI permit a choice of compounds appropriate for evaporative cooling, for example in electronic systems, or as convection cooling liquids in transformators or similar devices. Their minimum dielectricity constant, their high breakdown voltage, their ability for arc quenching at low decomposition rates, their low loss factors in high-frequency alternating fields and relatively low temperature dependence of their viscosity render the substances of different boiling ranges suitable for such applications in the electrical field. Their extraordinary dissolving power for oxygen and carbon dioxide enable them to be applied as an oxygen conveyor in heart-lung machines, and also directly as a blood substitute in living organisms.

The scope of the invention comprises also the partially fluorinated products III and IV, which are also novel aliphatic ethers. Their extraordinary technical interest resides above all in the possibility of their being applied as starting products for electrofluorination where, as already mentioned, they ensure the production of valuable perfluorinated products having considerably higher yields than those obtained on the basis of fluorine-free alkyl ethers having a comparable number of carbon atoms.

The use of partially fluorinated starting products not only has a favorable effect on the increase of yields, but also, because of decreased current and energy expenditure for cell cooling and HF condensation from the waste gases, on the profitability of the fluorination process.

Depending on the molecular weight, the products III and IV of the invention are colorless to light brown, highly viscous, mobile liquids which are only sparingly soluble in hydrofluoric acid. While preparing perfluoropropene adducts of aliphatic or cyclic alcohols, it has surprisingly been found that secondary alcohol functions also reacted quantitatively with the fluoro-olefin, when instead of metallic sodium an aliphatic trialkylamine was used as catalyst. As such amines, the following may for example be used: trimethylamine, triethylamine, tri-n-propylamine, tri-n-butylamine, N,N,N',N'-tetramethyl-ethylene-diamine, N,N,N',N'-tetramethyl-hexamethylene-diamine, or diazo-bicyclo-2,2,2-octane. The alcohol is dissolved in an aprotic, polar solvent, for example in acetonitrile or dimethyl formamide, and at least 0.1, preferably from 0.5 to 1 mole of a trialkylamine, for example triethylamine, is added per OH group to be converted. The perfluoropropene introduced is generally reacted under normal pressure and at a temperature of from $-30°$ to $+100°C$, preferably from $20°$ to $60°C$. For purification, the solution is washed with water, subsequently with diluted aqueous hydrochloric acid and, after a second washing with water, it is dried. A further purification is carried out by rectification in vacuo or by chromatography on neutral silica gel. The known reactions with $C_2F_4$ are carried out in the presence of metallic sodium as catalyst. The products obtained are characterized by analysis data, osmometric molecular weight determination and their IR— and H—NMR spectra.

The products are free from OH, but they contain small amounts of olefins having a $ROCF=CF-CF_3$ structure, the formation thereof being caused by splitting off of HF by the effect of the trialkylamine. The presence of such olefins does not substantially influence the course and the result of the electrofluorination, but it causes the formation of small amounts of perfluoro-methyl ethers (see Examples 1 and 2).

The electrofluorination of the perfluoro-olefin-alcohol adducts to form the perfluorinated ethers is carried out in a Simons cell of usual construction (see U.S. Pat. No. 2,519,983), which consists of a vessel of stainless steel having a cooling jacket containing a brine solution. The capacity of this vessel is of 1.5 liters, and it contains a package of electrodes consisting of 25 parallel nickel plates having a slit width of 2,5 mm and an anode surface of 30.8 dm². The cell is provided with a circulation pump for electrolyte, a condenser, and a washing tower for the absorption of HF from the waste gas.

The tests were always run for several days at voltages of from 4.0 to 7.5 V, current densities of from 0.2 to 3.0 A/dm², preferably from 0.5 to 2.0 A/dm², and electrolyte temperatures of from $-20°$ to $+30°C$, preferably from $0°$ to $+15°C$. The starting materials were introduced in amounts of from 3 to 20 weight %, preferably from 5 to 15 weight %, relative to the hydrofluoric acid. Since the products were insoluble in hydrofluoric acid at the start, an emulsification as far as possible by means of intense electrolyte circulation was very important. However, it was surprisingly observed that, a short time after the beginning of the electrolysis, the electrolyte was homogenized in the form of a genuine solution, which did not separate again. With progressive electrolysis, the perfluorinated crude product separated from the above solution. In order not to take off after-dosed starting material together with the final product, after-dosing was carried out always immediately after taking off the product.

The products obtained were washed with hot aqueous alkali lye in order to remove small amounts of hydrofluoric acid and perfluoro-carboxylic acid fluoride. After multiple washing with water and drying, the substances were fractionated. The substances were analyzed by gas chromatography and divided into their main components which, after isolation, were characterized in their structure by mass and F-19-NMR spectroscopy as well as analysis.

The following examples illustrate the invention:

EXAMPLE 1

I. Preparation of tris-hexafluoropropyl-glycerol ether 46 g of glycerol, 150 ml of triethylamine and 500 ml of acetonitrile were introduced into an autoclave having a capacity of 1 l and then condensed with 300 g of perfluoropropene. Without heating, the whole was shaken for 6 hours at room temperature, and the reaction mixture was worked up by distillation.

Yield: 200 g (81.2 % of the theor. yield, relative to glycerol used)

Boiling point: 82°–90°/4 torrs.

|  |  | C | H | F |
|---|---|---|---|---|
| Analysis: | calculated: | 26.6 | 1.47 | 63.1 |
|  | found: | 27.3 | 1.40 | 62.2 |

Molecular weight: calculated: 542 found: 509

II. Electrofluorination

A Simons cell was charged with 150 g of tris-hexafluoropropyl-glycerol ether and 1400 g of anhydrous hydrofluoric acid. Within 55 hours, a further 195 g of starting material were added, this addition being carried out in little portions with a several hour interval. The electrolyte temperature was a constant 0°C during the whole test. The voltage varied in a range of from 4.1 to 6.0 V, the latter value dropping with addition of material but being attained again after a few hours because of decrease of concentration, while a constant amperage of 30 A was maintained. After a total 60 hours, 173 g of perfluorinated product, corresponding to 39.4 % of the theoretical yield relative to the reaction equation, were obtained.

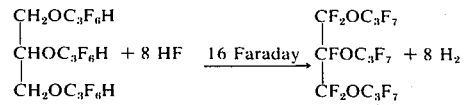

After a 4 hour alkaline treatment by boiling with 20 % aqueous KOH solution, 159 g of product washed and dried with calcium chloride were obtained, 81.0 % of which, according to the gas chromatogram, consisted of a uniform substance, the boiling point thereof being determinated at 162.6°C/760 torrs (corrected). The mass spectrum of the main component had a highest mass peak of very low intensity at m/e = 667, corresponding to M—F; the highest intense peak was at m/e = 567, corresponding to $M-C_2F_5$. The NMR spectrum proved the structure of the perfluorinated product as indicated in the reaction equation.

Analysis: calculated: 21.0 % C; 72.0 % F; 0.0 % H. found: 20.6 % C; 71.0 % F; 0.3 % H.

Furthermore, the following substance

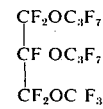

having a highest mass peak at m/e = 479, corresponding to M—(CF$_3$+2F) was found. The amount of this component in the crude product was 6.5 area %.

EXAMPLE 2

I. Preparation of the preliminary product erythritol-tetrakis-(hexafluoropropyl) ether 124 g of erythritol were dissolved in 800 ml dimethyl formamide, and 500 ml of triethylamine were added. When perfluoropropene was fed in, the temperature rose to 50°C. After absorption of 750 g of perfluoropropene, the reaction was complete, which showed in a decrease of the reaction temperature. The reaction mixture was shaken two times each with 1 liter of water, and two times with each 0.5 liter of HCl; the organic phase was neutralized with NaHCO$_3$ solution, washed again with water and dried over Na$_2$SO$_4$.

Crude yield: 660 g.
Yield after distillation 400 g (55.4 % of the theor. yield, relative to erythritol used.)
Boiling point: 83° – 95°/0.7 torr
Analysis: calculated: 26.6 % C; 1.4 % H; 63.1 % F. found: 27.9 % C; 1.6 % H; 60.7 % F.
Molecular weight: calculated: 722; found: 711 (osmometrically in benzene).

II. Electrofluorination

Within 44 hours, 328 g of fluorination product, corresponding to 67 % of the theoretical yield relative to the reaction equation, were obtained from 368 g of erythritol-hexafluoropropyl ether.

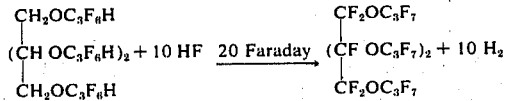

The electrolysis temperature was about 95°C, the voltage varied within the range of from 4.6 to 6.2 V and the amperage was 23.5 A on the average, corresponding to an average current density of 0.76 A/dm$^2$. The 209 g of product obtained after an alkaline treatment of refluxing for 3 hours, subsequent washing and drying, had a boiling range of from 126.7° to 243°C /760 torrs (corr.); the main fraction passing over at 195°C/760 torrs (corr.).

The substance showing as main component in the gas chromatogram by taking 38.2 area % was clearly identified as being perfluoro-erythritol-tetrapropyl ether by the mass spectrum m/e = 864 ≙ M—2F, and the F-19-NMR spectrum.

Analysis: calculated: 21.2 % C; 71.4 % F; 0 % H. found: 21.6 % C; 71.7 % F; <0.3 % H.

Furthermore, the crude product treated with alkali contains among others 12.1 area % of perfluoro-glycerol-tripropyl ether.

EXAMPLE 3

I. Preparation of sorbitol-hexakis-(hexafluoropropyl)ether 83 g of sorbitol were dissolved in 2 l of dimethyl formamide, and 1300 ml of triethylamine were added. After absorption of 600 g of perfluoropropene, the reaction temperature dropped from 52° to 28°C. Two times 2 liters of water were then added to the solution which was subsequently washed 3 times with HCl. In order to remove the HCl residues, the solution was again washed with 1 l of water and then dried over Na$_2$SO$_4$.

Crude yield: 375 g
Yield after distillation: 230 g (46,6 % relative to sorbitol used).
Boiling point: 135°–138°/0.3 torr

|  |  | C | H | F |
|---|---|---|---|---|
| Analysis: | calculated: | 26.6 | 1.29 | 63.2 |
|  | found: | 28.0 | 1.4 | 60.5 |

Molecular weight: calculated: 1082. found: 960 (osmometrically in benzene).

II. Electrofluorination

The electrolysis cell was charged with 10 g of sorbitolhexakis- (hexafluoropropyl) ether and 1400 g of anhydrous hydrofluoric acid. Within a total period of 86 hours, another 334 g of starting material were added in portions of from 20 to 30 g each. Before each such addition, as always in the processes described, fluorination product was removed from the cell and immediately examined by gas chromatography for the presence of starting material. When starting material was still present, the fluorination product was recycled. The average electrolysis temperature was 5°C, the average current density 0.6 A/dm$^2$; the voltage was maintained below 6.3 V and was 4.2 V at the start. After the usual alkaline treatment, 164 g of dried product were obtained from the fluorination product taken off the cell. This corresponds to 30.6 % of the theoretical yield relative to the following reaction equation:

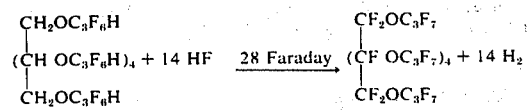

In the separation by distillation, the scarcely volatile main products passed over at a temperature in the range of from 90° to 142°C /<1 torr.. According to gas chromatography analysis, perfluoro-hexapropyl-sorbitol ether was the main component of the high-boiling fraction, taking 62 area %. The identity of the main component with the cited structure was proved by the F-19-NMR and mass spectra (highest peak at m/e = 1315 = M-F).

Analysis: calculated: 21.6 % C; 71.2 % F 0 % H. found: 22.0 % C; 70.5 % F <0.3 % H.

Among the secondary components, the following compounds were identified:

1) 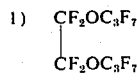

2) 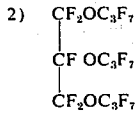

-continued

3) 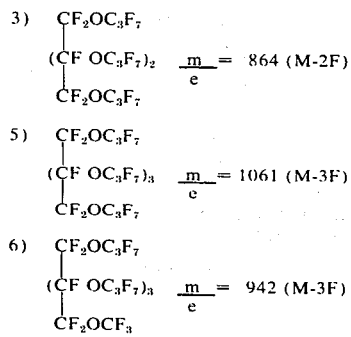

4) 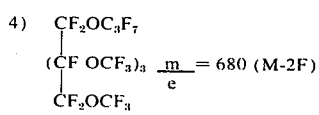

5) 
$$\begin{array}{c} CF_2OC_3F_7 \\ (CF\ OC_3F_7)_3 \\ | \\ CF_2OC_3F_7 \end{array} \quad \frac{m}{e} = 1061\ (M\text{-}3F)$$

6) 
$$\begin{array}{c} CF_2OC_3F_7 \\ (CF\ OC_3F_7)_3 \\ | \\ CF_2OCF_3 \end{array} \quad \frac{m}{e} = 942\ (M\text{-}3F)$$

EXAMPLE 4

In a repetition of the fluorination reaction described in Example 3, a solution of 350 g of sorbitol-hexakis-(hexafluoropropyl) ether in 150 g of perfluoroheptane was subjected for 53 hours to fluorination in the same cell. By this operation mode, the high viscosity of the starting material was substantially reduced. Fluorination was carried out at 0°C and a current density of 1.0 A/dm². The product to be fluorinated did not dissolve completely in the hydrofluoric acid. After the usual alkaline treatment, the perfluoroheptane solvent was distilled off at 80°–84°C; 118 g of fluorination product corresponding to 28 % of the theoretical yield remained, which product showed a similar quantitative composition as that of Example 3.

EXAMPLE 5

I. Preparation of dihexafluoropropyl-butyleneglycol ether 400 g of dibutyleneglycol were dissolved in a 6 L flask with agitator in 2.4 l of acetonitrile and 560 ml of triethylamine, and perfluoropropene was fed in until a weight increase of 1000 g was obtained. The reaction temperature was maintained at 45° to 50°C.
subsequently, the reaction mixture was poured into 3 l of icewater, the two phases were separated and the organic phase was washed two times with 2 liters each of water. In order to remove triethylamine still adhering, the organic phase was washed with 1 l of 1 m HCl, subsequently again with 1 l of water and then dried over $Na_2SO_4$.

Crude yield: 1050 g
Yield after distillation: 770 g (67.5 % of the theor, yield, relative to dibutyleneglycol used).
Boiling point: 100°–105°/0.03 torr

| | | C | H | F |
|---|---|---|---|---|
| Analysis: | calculated: | 36.4 | 3.9 | 49.3 |
| | found: | 37.3 | 3.4 | 48.4 |

Molecular weight: calculated: 462. found: 435 (osmometrically in benzene).

II. Electrofluorination 585 g of di-hexafluoropropyl-butyleneglycol ether were electrofluorinated in the cited cell. The process lasting 56 hours at an electrolysis temperature of 5°C, an average current density of 1.35 A/dm² and a voltage of from 4.9 to 6.4 V yielded 657.3 g of fluorination product, corresponding to 66 % of the theoretical yield relative to the reaction equation as follows:

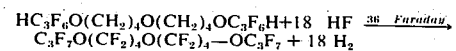

Besides 3 main components, the crude product contained 3 secondary components and a great number of trace components. After the alkaline treatment, the boiling range of the substance was from 175° to 203°C/760 torrs (corr.).

The perfluorinated analog of the starting substance took 39 area % of the chromatogram, and its F-19-NMR spectrum proved the expected structure. In the mass spectrum, the fragments $C_4F_8OC_3F_7$(m/e = 385) and $OC_4F_8OC_4F_7$(m/e = 413) were detected.

Analysis: calculated: 21.4 % C; 72.5 % F; 0 % H.
found: 21.4 % C; 71.8 % F; 0.3 % H.

As a further main component taking 20.0 area % of the gas chromatogram, the ether $C_3F_7O(CF_2)_4OC_4F_9$ was found, the structure of which was confirmed by the mass spectrum (highest masses m/e = 435 and 385, corresponding to M-$OC_3F_7$ and M-$C_4F_9$) and the NMR spectrum. As a further component taking 18.4 area %, perfluoropropyl-butyl ether $C_4F_9OC_3F_7$ was observed. Highest mass m/e = 385 ≙ M-F.

EXAMPLE 6

I. Preparation of
pentaerythritol-tetrakis-(hexafluoropropyl)ether

In a 2 l autoclave, 54 g of pentaerythritol, 800 ml of dimethyl formamide and 300 ml of triethylamine were condensed with 400 g of perfluoropropene. The whole was heated at 60°C for 20 hours, the reaction mixture was poured into 2 l of water and the solution was well shaken. The organic phase was again washed with 1 l of water and dried over $Na_2SO_4$. Triethylamine still present was removed by means of the vacuum pump.

Crude yield: 300 g
Yield after distillation: 167 g (57.2 % of the theor. yield, relative to pentaerythritol used).
Boiling point: 102°–107°/0.25 torr

| | | C | H | F |
|---|---|---|---|---|
| Analysis: | calculated: | 27.7 | 1.63 | 61.9 |
| | found: | 29.3 | 1.50 | 59.8 |

Molecular weight: calculated: 736. found: 697 (osmometrically in benzene).

17

II. Electrofluorination

As already described, 80 g of pentaerythritol-tetrakis-(hexafluoropropyl) ether were electrolyzed together with 1400 g of anhydrous hydrofluoric acid in the cited cell. Within 38 hours, further 217 g of starting material were added, so that after a total of 45 hours, at an average electrolysis temperature of 5°C, a current density of 0.95 A/dm$^2$ and a voltage of from 4.9 to 6.3 V, 297 g of the substance were converted. After the fluorination process was complete, 121 g of product, corresponding to 31 % of the theoretical yield relative to the following reaction equation were obtained.

$$C(CH_2OC_3F_6H)_4 + 12 HF \xrightarrow{24 \text{ Faraday}} C(CF_2OC_3F_7)_4 + 12 H_2$$

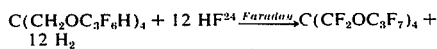

Boiling range of the product treated with alkali: 215°–226°C/760 torrs (corr.). The main component (73.5 area % of the gas chromatogram) had a highest mass peak at m/e = 833 $\hat{=}$ M —C$_2$F$_5$. The NMR spectrum proved the structure indicated in the equation.

Analysis: calculated: 21.5 % C; 71.9 % F. found: 21.7 % C; 71.0 % F.

Secondary product according to NMR and mass spectrum:

(m/e = 767 $\hat{=}$ M—F) : CF$_3$C(CF$_2$OC$_3$F$_7$)$_3$

EXAMPLE 7

200 g of bis-tetrafluoro-ethyl-(ethylene-diglycol) ether (prepared in known manner from ethylene-diglycol ether and tetrafluoro-ethylene; U.S. Pat. No. 2,409,274; refractive index h$_{18}$ = 1.343 colorless liquid) after fluorination in the same electrolysis cell for 36 hours at 0°C and at a current density of 0.6 A/dm$^2$, yielded 85 g of fluorination product, corresponding to 21.5 % of the theoretical yield relative to the reaction equation $$HC_2F_4C[C_2H_4O]_2C_2F_3H + 10 HF \xrightarrow{20 \text{ Faraday}} C_2F_5OC_2-F_4OC_2F_4OC_2F_5 + 10 H_2.$$

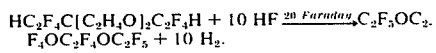

According to gas chromatography analysis, the product took 90 area % and had the following structure C$_2$F$_5$OC$_2$F$_4$OC$_2$F$_4$OC$_2$F$_5$. Its boiling range was from 75° to 100°C/760 torrs (corr.). The mass spectrum of the substance had the highest mass peak at m/e = 367 $\hat{=}$ M—F; the NMR spectrum confirmed the structure.

Analysis: calculated: 19.8 % C; 70.4 % F; 0 % H. found: 20.2 % C; 70.0 % F <0.3 % H.

What is claimed is:

1. A compound of the general formula

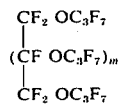

wherein *m* is from 1 to 4.

2. The compound perfluoro-erythritol-tetrapropyl ether.
3. The compound perfluoro-glycerol-tripropyl ether.
4. The compound perfluoro-sorbitol-hexapropyl ether.

* * * * *